United States Patent [19]
Wilson

[11] Patent Number: 6,106,295
[45] Date of Patent: Aug. 22, 2000

[54] HIGH DENSITY POLYETHYLENE VENEERED CROWNS FOR CHILDREN

[75] Inventor: George M. Wilson, Visalia, Calif.

[73] Assignee: GSF Trust, Visalia, Calif.

[21] Appl. No.: 09/370,899

[22] Filed: Aug. 9, 1999

[51] Int. Cl.[7] .................................................. A61C 5/08
[52] U.S. Cl. ....................................... 433/222.1; 433/218
[58] Field of Search ................................ 433/222.1, 218, 433/223, 206

[56] References Cited

U.S. PATENT DOCUMENTS

| | | | |
|---|---|---|---|
| 4,433,959 | 2/1984 | Faunce | 433/222.1 |
| 4,722,689 | 2/1988 | Corbett . | |
| 5,308,243 | 5/1994 | Emmons | 433/218 |
| 5,538,429 | 7/1996 | Mayclin | 433/222.1 |
| 5,624,261 | 4/1997 | Wiedenfeld | 433/222.1 |

FOREIGN PATENT DOCUMENTS

| | | | |
|---|---|---|---|
| 169552 | 1/1986 | European Pat. Off. | 433/222.1 |
| 2662070 | 11/1991 | France | 433/222.1 |
| 3435918 | 4/1986 | Germany | 433/222.1 |
| 1237197 | 6/1986 | U.S.S.R. | 433/218 |
| 2199751 | 7/1988 | United Kingdom | 433/222.1 |

OTHER PUBLICATIONS

Green et al, "Chairside Aesthetic Option for Anterior Stainless SteelCrowns", American Academy of Pediatric Dentistry, 1998, San Diego, California.

Tofuki et al, "Effect of Surface Preparation on the Bond Strength of Thermoset Resins to Stainless Steel," Journal of Pedodontics, Vol 9:77 (1984) p. 77–83.
Undated Brochure: "White Steel Crowns" (2 pages).
Undated Brochure: "The New Generation of Pedo Stainless Steel Crowns" (1 page).
1991 Brochure: "Welcome to the Wonderful World of Kinder Crowns" (1 pahge).
1993 Brochure: "The Whiter Biter Crown II" (1 page).
Undated Brochure: "Java Crown" (1 page).
Undated Brochure: "Nu Smile Primary Crowns" (1 page).

*Primary Examiner*—Todd E. Manahan

[57] ABSTRACT

An esthetic preformed crown for children which uses layers of a custom crown material applied as a veneer over non-precious, semiprecious and precious casting metals fabricated for the casting of custom copings and as an alternative to porcelain, vitrioids, copolyester, epoxy, and acrylics. The veneer is comprised of high density polyethylene, which is thermoformed over a screened preformed stainless steel crown to obtain the desired appearance. The crown material is specifically comprised of pigmented high-density polyethylene because of its high elastic limit great flexural strength, ability to withstand great shearing force when mechanically bonded to a preformed crown. The crown of the present invention has natural appearance of a vital tooth. The high density polyethylene veneer in this esthetic preformed crown has a greater bond strength than any current state of the art veneer or other facing material currently used on children's esthetic stainless steel crowns.

13 Claims, 1 Drawing Sheet

HIGH DENSITY POLYETHYLENE VENEERED CROWNS FOR CHILDREN

BACKGROUND OF THE INVENTION

1. Field of the Invention

This invention pertains to improvements in preformed crowns. More specifically, the invention is the application of a veneer over a stainless steel crown for children. The veneer is comprised of an esthetically pleasing material, which more closely matches color of the children's natural teeth, with the added benefit of being thin and yet having superior resistance to the stresses to which crowns are typically subjected.

2. State of the Art

Performed stainless steel crowns (SSCs) are still the preferred choice for whole or partial replacements of carious teeth in children. Dental composites provide an alternative, which resemble teeth, but lack the strength of a preformed SSC. Children with extensive caries, occlusions with deep anterior bites, or that bruxes (teeth grinding habits) need the strength of stainless steel crowns.

A typical SSC is constructed from a preformed base material crown 10 such as stainless steel which is placed in the mouth to cover a prepared tooth 12 as shown in FIG. 1. The prepared tooth 12 is shown as having its surface ground away sufficient for the placement of the crown 10 thereon. The scale of the teeth shown and the crown 10 to be placed thereon is for ease of illustration and should not be considered to be at the correct scale. Furthermore, the portion of the tooth 12, which has been ground away, is also for illustration purposes only.

As shown in FIG. 1, the base metal crown 10, which as shown for illustration purposes is not a molar, and therefore can be pictured generally as a flattened bowl which is formed in the shape of a tooth with an open end 16 for placement over the prepared tooth 12. Proper tooth preparation includes removing all caries and proper shaping of the remaining natural tooth 12 to receive the SSC 10. Therefore, the prepared tooth 12 is typically left in place in the mouth so that its root provides anchor in the jaw for the SSC. An esthetic SSC, however, also includes a veneer placed over the base metal 10. It is the veneer and the method of attachment of the veneer to the base metal, which is critical to the success of the esthetic SSC, and the subject matter of this patent.

The esthetic SSC is designed with several objectives in mind. One purpose is to hide the base material covering the natural tooth so that a more natural looking artificial tooth is seen. The esthetic SSC also makes contact with other teeth or dental work, as well as food items placed in the mouth. Consequently, the preformed crown with the veneer in place must be able to withstand great shearing stresses because of the contact with forces of occlusion.

Similarly, a bridge is an artificial tooth replacement, which spans a gap between natural teeth. Unlike the esthetic SSC, however, the bridge can be fixed or removed. The bridge is typically supported by natural teeth or roots adjacent to the space being filled by the bridge.

It was stated that the esthetic SSC or bridge structure (hereinafter referred to only as an esthetic SSC) is comprised of a veneer bonded to a base metal beneath. However, the veneer can have several layers, which exhibit different light absorption an reflective properties. The different properties are obtained by mixing the veneers with other materials. For example, many of the esthetic SSCs used today have a decidedly unnatural look to them. Some have the appearance of a flat paint, lacking any translucency of natural enamel. This makes the crown stand out and be very noticeable and visible.

The state of the art is replete with various tooth colored materials used as aesthetic veneers to ameliorate the silver crown smile that many people have difficulty accepting, especially children. Children are especially sensitive to their appearance, and their self-esteem can be profoundly affected by the comments of their peers who are quick to point out distinguishing features.

The majority of the materials used as veneers use dental composites that are bonded onto esthetic SSCs. The bonding process is also a major obstacle to reliable esthetic SSC construction because it is another place where failure of the esthetic SSC can occur. State of the art bonding can consist mechanically of sandblasting, welding of mesh, and making holes in the crown, as well as chemical retention using silanes, tin plating, or the use of bonding agents such as 4-meta. Another example is taught in U.S. Pat. No. 4,722,689 issued to Corbett, whereby epoxy is electrically deposited onto temporary crowns.

Another disadvantage of the prior art is that once a veneer or facing is fractured, the veneer typically continues to separate further, or the dental construct might break apart completely due to percolation at the interface between the veneer and the base metal.

All of the veneers and bonding methods described above suffer at least one serious inherent weaknesses such as bonding strength, staining, wear under abrasion, general unattractiveness or lack of esthetic consideration. It would therefore be an advantage over the prior art to create an esthetic SSC to be used in a child's mouth, which has the appearance of natural teeth while providing superior abrasion resistance. It would also be an advantage to bond a veneer to the base metal using a mesh or mechanical retention having the bond strength contingent upon welded stainless steel rather than upon the flexural strength or elastic limit of the material of the veneer. That is to veneer a material so strong, that the point of failure does not remain with the porcelain or plastic resin but with the failure of stainless steel mesh that is welded to the base metal. This is in fact a very superior bond of the veneer to the crown. Still another advantage, would be to have a veneer that does not degrade and chip away during its short life in the mouth as a restoration on a baby tooth.

OBJECTS AND SUMMARY OF THE INVENTION

It is an object of the present invention to provide a method and apparatus for creating an esthetic SSC, which can withstand relatively large shearing forces with respect to other material used in esthetic SSCs.

It is another object to provide a method and apparatus for creating an esthetic SSC for children.

It is still another object to provide a method and apparatus for creating an esthetic SSC which is more or equally natural appearing than other materials used in children's crowns.

It is yet another object of the invention to provide an esthetic SSC which is more fracture resistant than the crown material used in adult crowns. That is to have a material that has a high elastic limit or great flexural strength. Due to the fact that children are unable to cooperate as pertaining to adult use of dental appliances, they are more susceptible to aspiration of loose broken material in the mouth.

It is still another object of the invention to maintain color stability, and abrasion resistance which exceeds or is equal to other esthetic SSCs on the market.

In accordance with these and other objects of the present invention, it is the inventor's intention to create an esthetic SSC for children which uses layers of a crown material as a veneer over a base metal. The veneer is comprised of a crown in various stages to adjust the translucency and the whiteness of the preformed crown to obtain the desired appearance. The crown material is specifically known to the industry under the name high density polyethylene (HDPE). HDPE is used because of its desirable qualities of withstanding relatively large shearing stresses, as well as being able to bond to itself with great strength, and it may create the appearance of natural teeth.

The method of creating the preformed crown for children includes the steps of 1) preparing the surface of the base metal with a mesh screen upon which the veneer is to be thermoformed, 2) applying the first layer of veneer which is opaque to hide the metal 3) applying one or more successive layers of a milky translucent material to give a life-like appearance to the crown, and 4) finishing the veneer with rotary instruments to correctly contour the veneer. The layers of the veneer are applied with a very precise thermoforming that is sensitive to exact temperature of the melting point of HDPE.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Reference will now be made to the drawings in which the various elements of the present invention will be given numerical designations and in which the invention will be discussed so as to enable one skilled in the art to make and use the invention.

Figure 1:
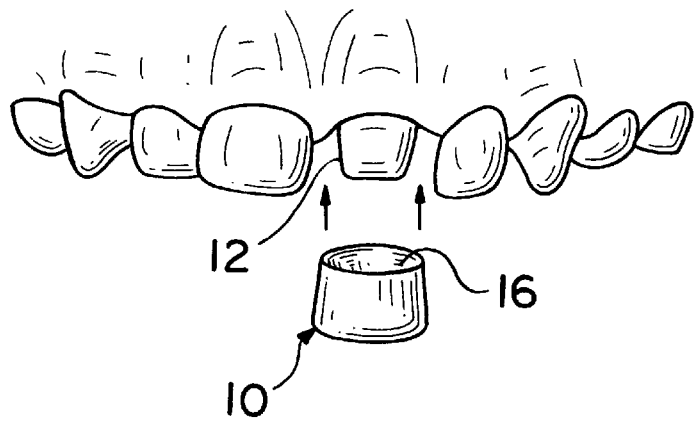
FIG. 1 illustrates where the preformed base metal crown 10 of FIG. 1 is placed on a tooth 12 which is prepared to receive it.
Figure 2A:
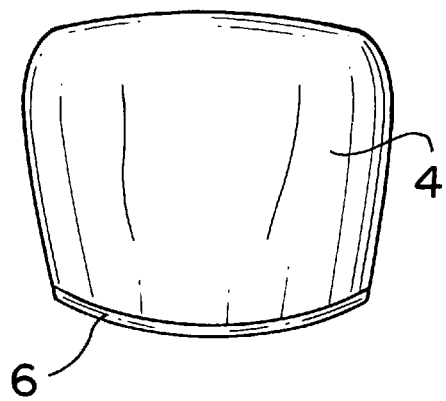
FIG. 2A is an elevational front (facial) view of an esthetic SSC.
Figure 2B:
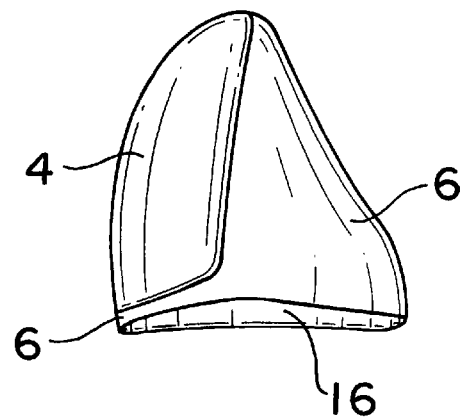
FIG. 2B is an elevational profile (interproximal) view of the esthetic SSC of FIG. 2A.
Figure 2C:
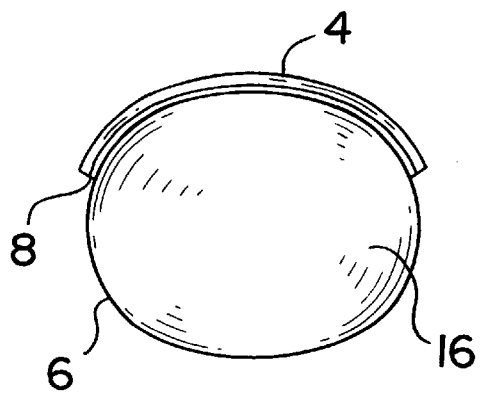
FIG. 2C is a bottom view of the esthetic SSC of FIG. 2A.
Figure 2D:
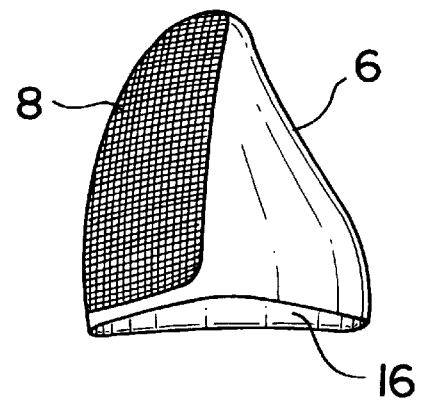
FIG. 2D is an the same view of 2B with the foundation of screen mesh to which is bonded the veneer.

FIG. 2A. is a facial (frontal) view of an esthetic SSC, showing the veneer 4 and the thin margin of base metal 6 at the cervical (bottom) margins. FIG. 2B shows an interproximal (side) view of an esthetic SSC. The facial surface of the crown is covered with a veneer 4 and the base metal 6 on the facial margin extends to the interproximal and the lingual (inside of mouth). The opening of the crown is shown below the lingual margin 16. FIG. 2C shows the view from the opening of the crown 16. The base metal 6 at the margin is ovoid, and the veneer 4 in the facial is elevated off the base metal on top of the illustration. FIG. 2D is another interproximal view showing the mechanical retention (screen mesh) on the facial as a foundation 8, to which is attached the veneer. The final veneer is displayed in the smile and not generally applied to any other surface not seen in the smile. It should also be remembered throughout that an esthetic SSC in the shape of a molar or any other tooth can be substituted for the illustrative esthetic SSC shown in FIGS. 2A, 2B and 2C. The embodiment herein described should not be considered limiting.

The present invention is comprised of a method of use for a product which falls under the classification of high-density polyethylene (HDPE). The material HDPE is unlike the ceramics, porcelains and other materials such as epoxy, dimethacrylate resin, ethyl vinyl acetate, sheet polyvinyl chloride and cross-linked sheet co-polyester (PETG), used in crowns and other dental constructs. The HDPE used in the construct of the present invention has tooth color pigments and other materials to facilitate the incorporation and dispersion of these pigments into the plastic resin.

It is the intention to teach the specific and heretofore unrecognized advantage of using HDPE as a crown material specifically in preformed crowns for children. This is because there are several problems, which the application of the crown material having the properties of HDPE uniquely solves. These problems include a weak bond strength of the construct to the base metal. Dental resin typically is rigid and brittle having, a low elastic limit. It chips easily at the resin/metal interface due to weak bond and flexural strength. These chips could at worst be aspirated by the child and at least appear unsightly. And then there remains the need to repeat the operation on an already anxious child. HDPE, on the other hand, once engaged by the mechanical retention, does not separate unless the mechanical retention is broken from its weld points. HDPE, aside from being tough, has a high elastic limit, and is compatible with the base metal. Thus chipping, crazing, and splitting is precluded at human mouth temperatures.

It was discovered that HDPE has properties which make it uniquely suited to the task of providing a preformed dental crown (or other dental construct such as a bridge, veneer, onlay, inlay, custom coping, jacket, etc.) for children. Specifically, it is because HDPE flexes and conforms much like the base metal. For example HDPE bonds particularly well to stainless steel mesh since it flows well when heated, completely encompassing a stainless steel mesh screen. The preformed base metal in a child's esthetic SSC is typically constructed of cold rolled stainless steel, thus assuring a strong bond welded to a stainless steel mesh screen. A strong bond between the preformed base metal and the veneer is critical for an esthetic SSC. However, the bond can be difficult to form between a hard, brittle material and a flexible metal crown. For that reason, the flexible mesh screen 8 and crown 6 are mated to semiflexible veneer material 4 to ensure a strong bond. Under these conditions, the effect of the combination of materials on stress forces is homogeneous. Consequently, peak loads are generally evenly distributed by the continuous transition of the HDPE and the preformed base metal. The tenacious polymer encompasses the micro-retentive areas of the screen mesh surface and resists debonding.

HDPE also has a high gloss and is polishable, resulting in a good imitation of natural teeth. Not all dental veneered crowns have this characteristic. The opaque layer component of HDPE is comprised of titanium dioxide and other colorants. With the application of successive translucent layers, the crown surface appears to have depth as a natural tooth, to the naked eye. Light is reflected and absorbed to create the appearance of vitality to the crown. The surface thus takes on a significant amount of luster typical of natural teeth.

It should also be stated explicitly that the dental construct of the present invention can take the shape and form of any of the constructs in which a veneer made of a polymerized resin might provide advantages over the state of the art. Typically, this applies to any application which can take advantage of high resistance to shearing forces.

A description of the veneer HDPE which is applied to the preformed base metal must include both a description of what different layers of the veneer are designed to accomplish, as well as a description of how the layers must be applied.

First, different layers are designed to both hide the preformed base metal as well as create an esthetically pleasing veneer which closely resembles the enamel of a natural tooth. Enamel has a translucent quality with a glassy finish. That same look can be simulated using HDPE by first applying an opaque layer (referred to as the opaque) which must be sufficiently dense to hide the base metal, but thin enough to enable the application of other layers without exceeding the size dimensions of the natural tooth structure being added thereto. However, because the preferred embodiment is for use with children, the opaque must be thin to fit properly.

Next in a preferred embodiment, a second veneer layer is applied. This second veneer layer is referred to as successive layers that are applied over the opaque. The successive layers appear translucent to achieve the enameled look of natural teeth.

It should be mentioned before continuing that although two layers of veneer have been described in a preferred embodiment, it that should not be considered limiting. One layer of tooth colored polymer may be applied to metal to achieve basic esthetics. The process of applying the veneer to the preformed base metal crown is disclosed as follows.

The method of veneer application begins with preparation of the base metal. All of the base metal that is to be covered with veneer needs a mechanical retention or more specifically a fine mesh stainless steel screen that is welded to the base metal crown. This layer of mechanical retention constitutes the interface of the base metal and the veneer inside of the opaque. As described above, a HDPE veneer layer is applied to the mechanical retention and base metal crown.

Next, the crown with the retention and the veneer are heated to the melting point of the polymer resin (HDPE). As the inside of the veneer melts into the mechanical retention a strong bond is made at the interface. The method by which the inventor might do this is with a narrow precisely heated stream of air from a heat gun on the veneer and the base metal. However, there are many ways by which heat may be precisely applied to the base metal and the veneer. The SSC maybe placed on a die and heated above the melting point of the resin in an oven before it is withdrawn to receive a preheated 0.020 sheet of HDPE, thus engaging the mesh.

Next, the successive layers may be applied by heating the polymer resin to the melting point, thus bonding each successive layer creating some translucency in the preformed crown. This is accomplished with skill and practice, but might be applied with advanced thermoforming, and injection molding techniques.

After the layers of polymer resin have cooled, the preformed crown may be finished, contoured, and polished with hand rotary instruments.

It is best that all heating be done electronically as any flame may ignite the polymer resin, rendering the appliance useless.

It is to be understood that the above described embodiments are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A dental construct useful in the repair and replacement of natural teeth in children comprising a metal base element preformed to fit at least one natural tooth to be repaired or replaced, said metal base element having at least one surface supporting mechanical retention means for securing a tooth-like veneer to said metal base element, and a tooth-like veneer secured to said metal base element by said mechanical retention means comprising at least one layer of high density polyethylene resin.

2. The dental construct described in claim 1, wherein said tooth-like veneer further comprises at least one color-modifying component compatible with high density polyethylene selected to give said veneer a natural tooth-like appearance.

3. The dental construct claimed in claim 2, wherein said dental construct is selected from the group consisting of custom copings, bridges and preformed crowns.

4. The dental construct described in claim 3, wherein said dental construct is a preformed crown.

5. The dental construct described in claim 1, wherein said tooth-like veneer comprises a first opaque layer of high density polyethylene in contact with said mechanical retention means and at least one additional layer of tooth-colored high density polyethylene in contact with said first opaque layer.

6. The dental construct described in claim 1, wherein said mechanical retention means comprises a metal mesh screen covering said at least one surface of the metal base element.

7. The dental construct described in claim 6, wherein said metal base element and said mesh screen are formed from a dental alloy.

8. The dental construct described in claim 7, wherein said dental alloy is cold rolled stainless steel.

9. A preformed, naturally-appearing crown for replacing a natural tooth in a child comprising a stainless steel crown base, a stainless steel mesh retaining element welded to a selected surface of the crown base, and a veneer of high density polyethylene covering the mesh on the selected surface of the crown base, wherein said veneer comprises a selected number of layers of high density polyethylene resin, at least one of said layers including a color-modifying component to impart a natural tooth-like appearance to said veneer.

10. A method of forming a selected dental construct useful in the repair and replacement of natural teeth in children, comprising the steps of:

(a) selecting a metal base element preformed to fit at least one natural tooth to be repaired or replaced in a child's mouth;

(b) attaching to at least one selected surface of said metal base element a mechanical retention element;

(c) applying at least one layer of high density polyethylene resin over said mechanical retention element to cover said at least one selected surface of said metal base element with said resin;

(d) heating said high density polyethylene resin-covered metal base element to the melting point of said high density polyethylene resin to bond the high density polyethylene resin layer securely to the mechanical retention element and the metal base element and form a veneer covering said metal base element;

(e) cooling the high density polyethylene veneer-covered metal base element; and (f) finishing, contouring and polishing the cooled high density polyethylene veneer-covered metal base element to form the selected dental construct.

11. The method described in claim 10, further comprising, before step d, the step of applying at least one additional layer of high density polyethylene resin to said at least one layer of high density polyethylene resin.

12. The method described in claim 11, further comprising, before step (c), the step of adding to said high density polyethylene resin at least one color modifying component selected to give the finished dental construct the appearance of a natural tooth.

13. A dental construct formed according to the method of claim 11.

* * * * *